United States Patent [19]

Benson, Jr.

[11] 3,992,326

[45] Nov. 16, 1976

[54] FUSED SALT COMPLEX OF ALUMINUM HALIDE AND MANGANOUS HALIDE DEPOSITED ON A CARRIER

[75] Inventor: Herbert L. Benson, Jr., Houston, Tex.

[73] Assignee: Shell Oil Company, Houston, Tex.

[22] Filed: July 3, 1975

[21] Appl. No.: 593,336

[52] U.S. Cl. ............................ 252/442; 260/683.75
[51] Int. Cl.² .......................................... B01J 27/10
[58] Field of Search .................. 252/442, 471, 463; 260/683.68, 683.75

[56] References Cited
UNITED STATES PATENTS 2,082,500  6/1937  Kuentzel ............................ 252/442

FOREIGN PATENTS OR APPLICATIONS 1,001,767  8/1965  United Kingdom ............ 260/683.68

Primary Examiner—G. J. Crasanakis

[57] ABSTRACT

A catalyst composition for hydrocarbon conversions such as paraffin isomerization is described which comprises a porous, refractory inorganic oxide carrier having deposited thereon a fused salt complex consisting of aluminum chloride and/or bromide and manganous chloride and/or bromide, said fused salt complex being formed by heating a composite mixture of the halide salts to a temperature above the melting point of the composite.

15 Claims, No Drawings

FUSED SALT COMPLEX OF ALUMINUM HALIDE AND MANGANOUS HALIDE DEPOSITED ON A CARRIER

BACKGROUND OF THE INVENTION

This invention relates to a supported acidic catalyst composition and various processes in which the catalyst can be employed to promote hydrocarbon conversion reactions especially useful in petroleum refining. More particularly, this invention is directed to a catalytic composition having superior stability in hydrocarbon conversions such as low temperature paraffin isomerization and paraffin alkylation, which comprises a fused salt complex of certain aluminum halides and manganous halides present on the surface of a porous, refractory carrier, and to its use in such hydrocarbon conversion processes.

Catalytic hydrocarbon conversion processes such as skeletal isomerization of isomerizable paraffins and cycloparaffins and ethylene alkylation of paraffinic hydrocarbons has long been recognized in the art. In the area of petroleum refining, processes such as paraffin isomerization have more recently acquired greater importance because of the need to maintain high octane ratings for motor fuels at the reduced levels of tetraethyllead or other organolead antiknock agents now mandated by environmental and legislative constraints. In this regard, isomerization of straight chain or slightly branched $C_5$ and $C_6$ paraffinic hydrocarbons to more highly branched hydrocarbons such as isopentane and dimethylbutane has been recognized as a viable alternative to the addition of lead compounds to motor fuel as a means of obtaining such high octane motor fuel.

The use of acidic hydrocarbon conversion catalysts of the Friedal-Crafts type in promoting isomerization and/or alkylation reactions is well known. In the case of paraffin or saturated aliphatic hydrocarbon isomerization, metal halides or mixtures of metal halides, e.g., aluminum chloride, aluminum bromide, zinc chloride, antimony cloride, etc., have generally been employed on a variety of refractory supports to effect isomerization of $C_4$ to $C_6$ hydrocarbons at temperatures ranging anywhere from 150° to 600° F, e.g., see U.S. Pat. Nos. 2,250,410 and 3,060,249. In such processes, a hydrogen halide is usually added along with the feed to act as a promoter or co-catalyst for the reaction while a hydrogen partial pressure is also maintained in the reaction zone to suppress undesired side reactions such as cracking of feed to lower molecular weight hydrocarbons and to prolong the catalyst life. To aid in suppressing these side reactions, it has been recognized that the catalyst composition, itself, can be modified via the incorporate of a hydrogenation component, e.g., platinum and platinum group metals, to impart a hydrogenation-dehydrogenation function along with the Friedal-Crafts activity, e.g., see U.S. Pat. Nos. 2,900,425, 2,924,629 and 2,999,074. Despite the numerous prior art disclosures dealing with such Friedal-Crafts catalysts, their acceptance on a commercial scale has not been outstanding in the area of paraffin isomerization. While the reasons for the limited commercial success of such catalysts are varied, some of the more substantial problems encountered include the requirement of higher reaction temperatures, e.g., 400° F or above, for adequate catalyst activity and the high rates of catalyst deactivation due to metal salt losses from the catalyst bulk and side reaction product, e.g., cracking, contamination of the catalyst. In the former case, higher isomerization reaction temperatures are undesirable because the formation of highly branched, high octane valuedimethylbutane is favored by low temperature, e.g., 200° F, operation. In the latter case, metal salt losses, especially aluminum halides, via volatilization from the catalyst often require that additional halide be added to the reaction zone on a continuous basis and even then the catalyst lifetimes are not of sufficient duration to be attractive on a commercial scale. Accordingly, it would be of advantage if a Friedal-Crafts type catalyst could be developed which has good activity at low temperatures yet is not subject to deactivation to the extent previously encountered. In this respect it would be especially desirable if a catalyst composition employing aluminum halides as the acidic hydrocarbon conversion component could be found in which the need to continuously add fresh aluminum halide to the reaction zone is minimized or avoided since this addition significantly increases the costs and complexity of the process.

DESCRIPTION OF THE PRIOR ART

Fused salt compounds or complexes formed by melting an admixture of manganous chloride or bromide with aluminum chloride or bromide, respectively, have been reported by Kendall, Crittendan and Miller in J. Am. Chem. Soc., 45, 963 (1923). While no definite compositional formula for the complexes or compounds was given in that article, the compositions were assigned a tentative stoichiometry of $2\ AlX_3 \cdot MnX_2$ based on molecular proportions (X indicating Cl or Br). In subsequent studies, complexes or compounds of divalent metal halides and aluminum halides including manganous halides have been assigned the tentative composition of $M\ (AlX_4)_2$ (M = metal, X = halide), e.g., see Belt and Scott, Inorganic Chem. 3, No. 12, 1785–1788 (1964) through this compositional formula has not been completely verified except in the case of $Co(AlCl_4)_2$ i.e., see Ibers Acta Cryst. 15, 967 (1962). According to the I.U.P.A.C. and other literature references, such as those described above, these compounds or complexes have been named both as substituted aluminates and as alanates, i.e., tetrahaloaluminates and tetrahaloalantes, respectively.

In the area of catalysis, there is no known teaching which attributes any significant activity specifically to the solid form of the fused salt complexes formed from manganous chloride or bromide and aluminum chloride or bromide; nor further, even any disclosure of their existance as solids on refractory carriers. In this regard, the most relevant prior art appears to be U.S. Pat. No. 2,360,699 which is directed to liquid phase hydrocarbon conversion, e.g., isomerization with a molten salt mixture containing halides of the Friedal-Crafts type, e.g., $AlCl_3$, combined with anyone of a large number of other metal halide salts including manganese. However, in that patent teaching the hydrocarbon conversion reactions are carried out in a fluidized bed at a temperature above the melting point of the salt mixture such that the catalyst remains in the molten form while in contact with the reaction mass.

SUMMARY OF THE INVENTION

It has now been found that the fused salt complexes of certain manganous halides and certain aluminum halides, i.e., chlorides and/or bromides, when deposited on porous, refractory inorganic oxide carriers provide solid catalytic compositions having high activity in hydrocarbon conversion reactions such as isomerization of alkylation combined with very low rates of catalyst deactivation due to metal salt loss and side reaction contamination of catalyst. In fact, it appears that use of the instant catalysts in process such as low temperature isomerization will afford catalyst lifetimes in excess of one year without employing aluminum halide makeup and scrubbing facilities traditionally associated with the use of volatile aluminum halide salts in such processes.

Accordingly, in its broadest aspects, the instant invention provides a solid catalytic composition suitable for use in hydrocarbon conversion reactions which comprises a fused salt complex of an aluminum halide selected from the class consisting of aluminum chloride, aluminum bromide and mixtures thereof and a manganous halide selected from the class consisting of manganous chloride, manganous bromide and mixtures thereof present on the surfaces of a porous, refractory inorganic oxide carrier, said solid catalytic composition being formed by heating a composite mixture of the halide salt components of the fused salt complex to a temperature above the melting point of the composite, depositing the melted composite on the carrier surfaces and cooling of the carrier containing the melted composite to a temperature below the melting point of the fused salt complex. Also within the scope of the invention are those hydrocarbon conversion processes, i.e., low temperature isomerizatin of paraffinic hydrocarbons, in which the novel catalytic compositions according to the invention find particular application.

Further, according to the invention, it has also been found that a hydrogenation component such as metals from Group VIII of the Periodic Table of Elements can be advantageously incorporated into the catalyst composition of the invention to give it a stability-enhancing hydrogenation function in combination with its acid function. Accordingly, an additional aspect of the instant invention comprises the catalytic compositions described above wherein the carrier is also impregnated with metal hydrogenation component.

DESCRIPTION OF THE PREFERRED EMBODIMENTS

The catalyst compositions according to the invention are solid, supported acidic hydrocarbon conversion catalysts of the Firedal-Crafts type wherein the acid-acting function is a fused salt complex formed by heating a mixture of aluminum halide and manganous halide to a temperature above the mixture, said metal halide salts being selected from the class consisting of chloride, bromide and mixtures thereof. These catalyst compositions can be prepared by anyone of several techniques, it being essential only that the mixture of metal halide salts forming the fluid salt complex be heated to at least the point of fusion, i.e., melting point of the mixture, and deposited on the carrier while in this liquid or semi-liquid melted state. One suitable technique employed to prepare catalyst compositions according to the invention involves an initial step to form the fused salt complex by mixing together the metal halide salts in the desired proportions under application of heat until a uniform melt is obtained, followed by a subsequent deposition step wherein the carrier is contacted by the preformed melt in a conventional manner to deposit the desired quantity of fused salt on the carrier surface. In another technique, which is preferred because of its simplicity and ease of operation, the desired proportions of each metal halide salt and carrier are combined in a physical mixture and heated under mixing to at least the fusion point of the salt mixture whereby the fused salt complex obtains sufficient fluidity to uniformly impregnate the carrier particles. After deposition of the melted or molten salt complex on the surface of the carrier by either of the above techniques, the carrier containing the molten salt complex is subsequently cooled to a temperature at which the melted salt complex freezes or becomes solid via any conventional procedure, such as fluidization with a cooling gas, which prevents agglomeration of the catalyst particles. In either preparation technique, the metal halide salt starting materials are suitably employed in particulate form, e.g., powders, granules, etc., of a size convenient for mixing and melting in conventional equipment. To avoid hydrolysis, oxidation and/or other reactions involving the metal halides, which might otherwise deactivate the catalyst, e.g., carbon contamination, the catalyst preparation is suitably carried out under anhydrous conditions in a vacuum of atmosphere of hydrogen or inert gas such as nitrogen.

The specific temperature to which the mixture of metal halide salts must be heated to obtain the fused salt complex according to the invention will depend largely on the particular halide salts employed and the proportions in which the two metal halide salt components are combined in the metal salt composite. As a general matter, the proportions of the two metal halide salts which are suitably combined in a melted composite to obtain the fused salt complex of the invention range from 3:1 to 1:3 manganous halide to aluminum haide, expressed as parts by weight in the melted composite. To fuse or completely melt composite mixtures of the two metal salts falling in this general range, it is necessary to employ temperatures in the range of 300° to 1200° F with the higher temperatures in the range reflecting increased proportions of the manganous halide salt. For the bromide salts or salt mixtures which are predominately bromides (rather than chlorides), the weight ratio of manganous halide to aluminum halide preferably ranges from 2:1 to 1:3 and the corresponding temperature range required for melting of the salt composite suitably ranges from 300° to 800° F; brom ide salts having lower fusion temperatures than the chloride salts. For the chloride salts, which are preferred from cost and effectiveness standpoints in the invention, the weight ratio of manganous chloride to aluminum chloride suitably ranges from 2:1 to 1:2 in the melted composite with temperatures in the range of 400° to 1,000° F being required for fusion of the composite. Most preferably the fused salt complex according to the invention is made up of manganous chloride and aluminum chloride which are melted together in a weight ratio of 1.5:1 to 1:1.5 of $MnCl_2$:$AlCl_3$.

The metal halide starting materials for preparation of the fused salt complex according to the invention are suitably substantially pure and essentially free of deactivating impurities such as water. These pure halide salts are available from commercial suppliers or, in the alternative, can be prepared from relatively impure materials via conventional techniques, e.g., sublimation, recrystallization and drying, etc.

The carrier material employed in the catalytic compositions of the present invention is a porous, refractory inorganic oxide. This carrier is suitably of particulate form and may be of any desired shape such as spheres, pills, cakes, extrudates, powders, granules, etc. Preferably the carrier is porous and adsorptive in nature having a high surface area, e.g., 25–500 m²/g. Suitable refractory inorganic oxides include alumina, magnesia, boria, thoria, titanium dioxide, zirconium dioxide, chromium oxide, zinc oxide, silica-alumina, silica-magnesia, chromia-alumina, alumina-boria, etc. More preferably, the carrier is an alumina-containing material having a surface area in the range of 150–500 m²/g. Suitable alumina-containing materials are the crystalline aluminas known as the gamma- eta- amd theta-aluminas, though the presence of minor amounts of other well-known refractory oxides such as silica, magnesia, thoria, etc., is not precluded in this preferred class. Most preferably, the support is a substantially pure gamma-alumina having a surface area in the range of 150–300 m²/g. Prior to utilization in the catalyst compositions of the instant invention, it is preferred that the carrier be subjected to a treatment such as drying or calcinattion to assure that it is substantially free of entrained water. For alumina-containing carriers it is particularly preferred that the carrier be subject to calcination at a temperature of from 800° to 1,200° F for 2 to 24 hours prior to use.

When the catalysts according to the invention are employed in promoting paraffin isomerization, it has been found that catalyst activity can be enhanced, if the catalyst support is chlorided prior to deposition of the fused salt complex thereon. This pre-chloriding of the support which is particularly applicable to the preferred alumina-containing minerals of the invention can be carried out by a variety of techniques. One method which is suitably employed involves impregnating the support with an aqueous solution of hydrochloric acid, ammonium chloride, or metal chloride salt followed by drying at 200° to 300° F in air for 2 to 24 hours and thermal treatment in a hydrogen atmosphere at 500° to 1,000°F for 2 to 24 hours. Another suitable pre-chloriding technique involves pretreatment with aluminum cloride by mixing the alumina-containing support with substantially pure aluminum chloride and then heating to 400° to 600° F in a static system. In any case, it is preferred that the pre-chlorided support contain 0.5 to 5% by weight chloride ion based on support weight.

As indicated previously, it has also been found to be advantageous to incorporate a hydrogenation component into the catalyst compositions of the invention. Suitable hydrogenation components include metals from Group VIII of the Periodic Table of Elements, with nickel, cobalt and platinum being preferred. These metal hydrogenation components can be incorporated into the catalyst compositions according to the invention by any conventional technique and are preferably present only as a minor proportion of the total catalyst composition, e.g., 0.1 to 10% by weight of the finished catalyst. One suitable technique for incorporation of the metal hydrogenation component involves impregnation of the support prior to the deposition of the fused halide salt complex with an aqueous solution of the metal in cationic form, said metal cations being present in a metal compound selected from the class consisting of oxides, nitrates, acetates and halides. Preferably, the amount of solution used in this impregnation technique is just sufficient to completely wet the surface and pores of the support. After impregnation the carrier is preferably dried at a temperature of from 200° to 300° F for 2 to 24 hours and activated by calcination in a hydrogen atmosphere at a temperature of from 500° to 1,000° F for 2 to 24 hours. This dried and reduced carrier is then in a suitable form for deposition of the fused salt complex according to the procedure described above.

The catalyst compositions prepared as described above are particulate solids which can be employed directly to promote hydrocarbon conversion reactions such as isomerization and alkylation. The amount of fused salt complex employed in the catalyst compositions of the invention can vary quite widely depending on the particular use sought to be made of the catalyst. Generally, effective catalysts are obtained when the fused halide salt complex makes up about 10 to about 60% by weight of the finished catalyst (carrier plus fused salt and optional hydrogenation component). For catalysts employing fused salt complexes in which the halide anion is bromide, it is preferred that the fused salt comprise 40–60% by weight of the finished catalyst because of the higher molecular weight of bromide vs. chloride. For the preferred fused chloride salt complexes of the invention, substantial catalyst activity can be achieved with catalyst compositions containing about 10 to 50% by weight fused salt complex based on finished catalyst weight, with fused salt concentrations in the range of 20 to 40% by weight being most preferred.

Throughout this specification the catalyst compositions according to the invention have been described as being supported fused salt complexes or compounds of manganous bromide or chloride and aluminum bromide or chloride which are formed by melting together a composite mixture of the metal halides and depositing the melted composite on the surfaces of a carrier. While there is abundant evidence that the fused salt is substantially in the form of a chemically-combined double salt complex or compound on the carrier surface, it has not yet been possible to assign with certainty any definite molecular makeup to the active form of the fused salt. In view of the prior art teachings (see above), it appears likely that the fused salt is predominantly in the form of a tetrahaloaluminate or alanate since aluminum halides and manganous halides appear to combine chemically in a 2:1 molecualr ratio on melting, at least to the extent the reaction stoichiometry is satisfied. However, it is possible to obtain very stable catalysts which are active in promoting hydrocarbon conversion reactions by combining weight ratios of the two metal halides which are in substantial variance from the assigned 2:1 molecular ratio. This high catalyst stability which is attributable to both reduced volatility of the aluminum halide and moderation of the inherent catalytic activity of aluminum halide is indicative of chemical interaction between the two metal halides. In the latter case, it is postulated that the manganese ions are inserted in some fashion between the aluminum ions in the solid halide structure since the high stability and moderated activity of the instant catalysts, as compared to supported aluminum halides, can best be explained by a spreading out or separation of the active aluminum halide catalytic sites in the molecular structure of the catalyst. Further, it is known from other prior art teachings that deposition of a metal halide, such as aluminum chloride, on the surface of a carrier having chemically combined hydroxyl groups, such as the inorganic oxide carriers of the instant invention, will result in a reaction between chloride and hydroxyl groups to yield M-O-AlCl$_2$ centers wherein M is the inorganic oxide cation e.g. see U.S. Pat. No. 3,705,111. Thus, it is possible even in cases where the melted salt composite is present in a 2:1 AlX$_3$:MnX$_2$ (X = halogen) molecular ratio, that a certain amount of the fused salt mass may not exist in the manganous tetrahaloaluminate form previously postulated. Accordingly, for purposes of the instant description the term fused salt complex or compound is intended to encompass those mixtures of manganous halide salts and aluminum halide salts which, on fusion, afford the aforementioned complex-like properties, with recognition being given to the fact that the predominant complex form is very likely a manganous tetrahaloaluminate.

The catalyst compositions of the invention are particularly effective in promoting the isomerization of less branched paraffinic hydrocarbons to more branched paraffinic hydrocarbons. In this process application the catalyst compositions of the invention possess certain advantages over previously known supported Friedal-Crafts type catalysts in that they possess sufficient activity to effectively promote the isomerization reaction at low temperature while at the same time exhibiting superior stability under isomerization reaction conditions. This latter desireable property is believed to be a primary function of the manganous halide component of the fused salt complex in both reducing the volatility of the aluminum halide (and consequent salt losses) and suppressing the cracking activity inherent in the acidic aluminum halide function. Extensive cracking of the hydrocarbon feed in the isomerization process is, of course, undesireable because it leads to deposition of carbonaceous material on the catalyst surface and ultimately results in catalyst deactivation. In general terms, the isomerization process according to the invention involves conversion of less branched paraffinic hydrocarbons by contacting said less branched hydrocarbons e.g., normal paraffin hydrocarbons in the C$_4$ to C$_7$ range, in the vapor phase, in the presence of hydrogen and a hydrogen halide, with the supported, fused halide salt complex catalyst of the invention at a temperature in the range of about 180° to about 250° F. Preferably, the isomerization process according to the invention consists in vapor phase contacting of normal paraffin hydrocarbons of from 5 to 7 carbon atoms with the fused halide salt catalyst compositions of the invention at a temperature in the range of 180° to 235° F in the presence of hydrogen and a hydrogen halide selected from the class consisting of hydrogen chloride and hydrogen bromide, said hydrogen being present in the vapor phase at a mole ratio of about 1 to 10 based on the hydrocarbon feed and said hydrogen halide being present in gaseous form at a concentration of 1–20% by weight of the total vapor phase.

As a practical matter is is contemplated that the isomerization process according to the invention will find its widest application in upgrading the octane number of light saturate streams utilized in conventional refinery operation for gasoline manufacture. This paraffinic hydrocarbon feedstock will, most preferably, be debutanized and consist principally of C$_5$ and C$_6$ straight chain saturated hydrocarbons i.e. normal pentanes and hexanes. In addition, this preferred feedstock may also contain substantial amounts of isopentane or 2-methylpentane or mixtures thereof, as well as minor quantities of C$_6$ naphthenic hydrocarbons such as methylcyclopentane and cyclohexane. Since naphthenic hydrocarbons tend to suppress the isomerization activity of the catalyst, it is preferred that they comprise no more than about 5% by volume of the hydrocarbon feedstock and, most preferably, about 0.1 to 2% by volume of the total hydrocarbon feedstock. Napthhenes, however, can be beneficial for moderating very high activity on start-up or for operating at severe conditions. For isomerization of this C$_5$/C$_6$ paraffinic hydrocarbon feedstock in the process according to the invention, reaction zone temperatures in the ranges of 200° to 230° F seem to provide the optimum combination of high catalyst activity and selectivity and long catalyst lifetimes. For these reasons, the C$_5$/C$_6$ paraffinic hydrocarbon isomerization is most preferably carried at temperatures in the 200° to 230° F range.

As was noted above, the isomerization process according to the invention is carried out in the vapor phase in the presence of hydrogen and a hydrogen halide. The hydrogen halide which is suitably hydrogen bromide or hydrogen chloride acts as a promotor or co-catalyst for the isomerization reaction. From cost, availability and effectiveness standpoints it is preferred to employ hydrogen chloride in this application; however, when metal bromide salts are utilized to make up the fused salt complex of the invention, it is desirable to employ hydrogen bromide as the co-catalyst to avoid replacement of bromine in the solid catalyst phase with chlorine. However, active catalysts can also be obtained by using HCl with an MnBr$_2$/AlBr$_3$-on-alumina catalyst. While good isomerization activity can be obtained in the process of the invention when the hydrogen halide concentration in the vapor phase in contact with the catalyst is in the preferred range, mentioned above, i.e., 1 – 20% by weight hydrogen halide, it is most preferred to employ hydrogen halide concentrations of from about 5 to about 15% by weight of the total vapor phase. In this manner the catalyst activity is controlled at a reasonable level for practical operation. The presence of free or molecular hydrogen is important in suppressing undesired side reactions such as cracking which might otherwise adversely effect the catalyst life. Since high concentrations of hydrogen tend to inhibit the isomerization activity of the catalyst, the quantity of hydrogen added to the vapor phase of the catalytic reaction zone should not exceed 10 moles per mole of hydrocarbon reactant feed, said hydrogen preferably being present at a mole ratio of about 1 to 10 based on the hydrocarbon feed. Most preferably, the hydrogen is present at a mole ratio of 2.5 to 5 based on hydrocarbon feed. The hydrogen and hydrogen halide can be added to the vapor phase of the isomerization reaction zone in any conventional manner; however, they are preferably mixed with the hydrocarbon reactant prior to its introduction into the reaction zone to ensure uniform operation.

The isomerization process according to the invention may be conducted in any conventional manner, i.e., batch type of continuous operation employing the catalyst in a fixed bed, moving bed or fluidized bed system. For economic and practical reasons it is preferred to carry out the process continuously in a fixed catalyst bed system. The apparatus employed in this preferred operation may be of a conventional nature such as a vertical column containing the fixed bed catalyst through which the reacting hydrocarbons are circulated, with an external recycle line to send the reactants back through the bed any number of times. In this continuous system, reactant flow rates of from about 0.1 to 2 WHSV based on total vapor phase mixture throughput may be suitably employed. In any case, the reactant residence time in the reaction zone is dependent to a substantial degree on the severity of the reaction conditions including temperatures, hydrogen halide concentration and hydrogen partial pressure and the particular use sought to be made of the process. These factors are well known to one skilled in the art and need not be further detailed herein.

The reaction zone pressure employed in the isomerization process according to the invention is not considered to be critical and may vary over a rather wide range e.g., 200 to 500 psig. In cases where the low temperarture isomerization of a $C_5/C_6$ paraffinic hydrocarbon feedstock having the above described composition is carried out, it is preferred to mantain the reaction zone pressure in the range of about 300 to about 350 psig.

As indicated previously, the catalyst compositions of the invention exhibit very low rates of catalyst deactivation and superior lifetimes when employed for isomerization of paraffinic hydrocarbons. This is particularly true for the supported catalyst compositions employing a fused salt of manganous chloride and aluminum chloride. However, even the fused chloride salt catalysts will slowly decline in activity with use and at some point the activity will no longer be acceptable. As a means of dealing with this unacceptably low activity, a method has also been developed whereby the deactivated catalyst can be regenerated to an activity level approximating that of a freshly prepared catalyst. In basic terms, this regeneration process involves stripping and cracking of residual hydrocarbons on the catalyst surface with molcular hydrogen and a gaseous mixture of hydrogen chloride and molecular hydrogen at high temperature followed by high temperature treatment with hydrogen chloride alone. To carry out this regeneration process it is necessary to first discontinue flow of the isomerization reaction feed over the catalyst. After reactant flow is stopped the catalyst is then stripped with a flowing stream of hydrogen for 8 to 24 hours at a temperature in the range of 180° to 250° F. This initial stripping step removes substantially all of the volatile hydrocarbon present in the catalyst. Following removal of volatile hydrocarbons, the temperature of the catalyst is increased to a temperature in the range of 400° to 500° F and stripped with a gaseous mixture of hydrogen and hydrogen chloride at about 0.15:0.25 weight ratio for 8 to 12 hours. This second stripping step effects cracking and removal of residual hydrocarbons present on the catalyst. Finally to complete activation of the catalyst, the flow of hydrogen gas is stopped while the flow of hydrogen chloride gas is continued for another 4 to 8 hours at the same temperature range. After treatment with hydrogen chloride, the catalyst can be cooled to the isomerization process temperature, e.g., 180°–250° F and swept with a hydrogen-containing gas for 1 to 4 hours to remove excess hydrogen chloride prior to use in isomerization. Since water may adversely effect the catalyst, it is preferred that all steps of the regeneration process be carried out under substantially anhydrous conditions. Aluminum halide may be added as part of the regeneration procedure.

Preparation of catalysts according to the invention and their use in hydrocarbon conversion reactions will be further described by the following illustrations which are not to be construed as limiting the invention.

Illustrative Embodiment I
Catalyst Preparation

The catalysts according to the invention were prepared utilizing commercially obtained gamma-alumina carriers in the 40–80 mesh size range which had been calcined at 800° to 1000° F for 2 to 4 hours. Representative physical properties for these calcined alumina carriers include surface area of from 190 to 253 $m^2/g$, pore volumes of from 0.62 to 0.80 $cm^3/g$ and percent of pore volume in pores over 350 A diameter ranging from 2.5 to 11.1%. To improve the activity of the final catalyst composition the alumina carriers or supports were chlorided by either of two different techniques. In the first technique employed, the alumina selected was impregnated with an aqueous solution of hydrochloric acid (3.56% by weight) in a weight ratio of 1.16 part alumina to 1.00 parts HCl solution. This impregnated alumina was then dried for about 1.00 parts HCl solution. This impregnated alumina was then dried for about 17 hours at 250° F in air and then heated at atmospheric pressure in a flowing stream of hydrogen at 500° F for 1 hour and at 900° F for 2 hours. The final product analysis showed 1.6% by weight Cl. In the second technique, which also functioned to impregnate the support with a hydrogenation component, the alumina selected was impregnated with an aqueous solution of nickel chloride (26% by weight) in a weight ratio of 1.05 part alumina to 1.00 parts solution. This impregnated preparation was then dried and heated under flowing hydrogen according to the procedure previously described. The final product analysis in this case showed 4% by weight Cl.

Three different preparative techniques were utilized to deposit the fused halide salt complex of the invention on the surfaces of the alumina supports obtained, as above. The first of these techniques involved formation of the catalyst in place by melting of the fused salt complex starting materials in the presence of the support. The second technique encompassed pre-formation of the complex and subsequent deposition in melt form on the support. In the third technique, the alumina support was pre-impregnated with an aqueous solution of the manganous halide salt and the complex formed in situ by heating the aluminum halide in the presence of the impregnated support to the melting point of the fused salt complex. These techniques are segregated for convenience below under methods A, B and C subheadings.

Method A

The support (alumina) and catalyst salt complex precursors (manganese chloride or bromide and aluminum chloride or bromide) in powder form were mixed under anhydrous conditions and charged to a tubular reaction zone and heated in place under an initial hydrogen pressure of 350 psig at 450° F for 1 hour and then at 650° F for 2 hours. The 650° F temperature was sufficient to assure fusion of the metal halide salt precursors into the fused salt complex of the invention. After heating at 650° F for 2 hours, the reactor was cooled to 220° F and the catalyst (now in solid form) purged with hydrogen gas for 17 hours at this temperature. In a second modification of this technique, the reactor temperature was dropped to only 450° F and the catalyst was treated with an $HCl/H_2$ stream for 2 hours (reactor pressure of 350 psig) prior to purging with hydrogen at 220° F as described above. Catalysts prepared according to this technique included the following:

| % by wt. Cl on alumina | Aluminum halide Precursor | Manganous halide Precursor | Fused Salt Complex Weight Ratio Manganous halide | Fused Salt Complex Weight Ratio Aluminum halide | % by wt. in finished catalyst |
|---|---|---|---|---|---|
| 1.7 | AlCl₃ | MnCl₂ | 1/1 | | 18.4 |
| 1.6 | AlCl₃ | MnCl₂ | 1.34/1 | | 28.3 |
| 1.5 | AlCl₃ | MnCl₂ | 1/1 | | 31.1 |
| 4.0 | AlCl₃ | MnCl₂ | 1/1 | | 18.4 |
| 0 | AlBr₃ | MnBr₃ | 1/2.87 | | 52.8 |

Method B

Weighed quantities of powdered catalyst salt complex precursors (manganous chloride or bromide and aluminum chloride or bromide) were mixed and heated together in a reactor under anhydrous conditions at 450° F for 1 hour and 650° for 2 hours. The resulting melt was cooled to ambient temperature and ground to a fine powder under anhydrous conditions. This fine powder was then used in formulating catalysts in place of the powdered catalyst precursors in the procedure described under Method A above. Catalysts prepared according to this technique include the following:

A catalyst prepared essentially by the procedure described in Method A of Illustrative Embodiment I was tested for activity in isomerizing a typical $C_5/C_6$ paraffinic hydrocarbon feed in a 0.75 inch O.D. tubular microreactor. This catalyst, which was prepared in situ in the tubular reactor, consisted of 18.4% by weight $MnCl_2/AlCl_3$ salt complex on a gamma-alumina support, basis finished catalyst, wherein the metal halide salt complex was formulated utilizing an $MnCl_2/AlCl_3$ weight ratio of unity. The support also contained 10% by weight Ni and 1.8% by weight Cl as a result of being impregnated with an aqueous $NiCl_2$ solution as previ-

| % by wt. Cl on Alumina | Aluminum halide Precursor | Manganous halide Precursor | Fused Salt Complex Weight Ratio Manganous halide | Fused Salt Complex Weight Ratio Aluminum halide | % by wt. in finished catalyst |
|---|---|---|---|---|---|
| 1.7 | AlCl₃ | MnCl₂ | 1/1 | | 25.3 |
| 0 | AlCl₃ | MnCl₂ | 1/2 | | 40 |

Method C

The alumina support (0% by wt Cl) was impregnated with an aqueous solution of $MnCl_2$ (61.12g $MnCl_2$/100 ml solution) in a ratio of 68 ml of solution/100g alumina. This impregnated alumina was allowed to stand 0.5 hr. at room temperature and then dried at 250° F for 2 hours. Calcination was at 900° F for one hour under a stream of nitrogen. A catalyst was prepared from a portion of this alumina by adding 5.2g of $AlCl_3$ to 20g of the alumina cntaining manganese chloride which after mixing well was further mixed in a glass-lined autoclave by rotating the autoclave for 2 hours under 25 psig of $H_2$ at 410° F. The catalyst prepared by this technique contained 40% by weight fused salt complex based on finished catalyst with a weight ratio of 1.1/1 manganese chloride/aluminum chloride in the salt complex.

Illustrative Embodiment II ously described. Prior to introduction of the isomerization reaction feed, the catalyst was maintained under a hydrogen atmosphere at the approximate temperature desired for isomerization. To effect isomerization, a mixture of hydrocarbon feed, HCl co-catalyst and $H_2$ were passed over the catalyst in the vapor phase at a start-up temperature of 220° F. Other specific start-up conditions included a reactant feed rate of 0.25 WHSV, a reaction zone pressure of 350 psig, an $H_2$/hydrocarbon (oil) mole ratio of 10 and 5% by weight concentration of HCl in the feed. No aluminum chloride was added to the feed during the test. Throughout the test, the reactant composition and other reaction variables were altered to compensate for variations in catalyst activity and deactivation rates. The results of this test run, including the pertinent reaction variables are summarized in Table I below.

Table I

| Time, hrs. after start | 300 | 500 | 950 | 1700 | 1750 | 1925 | 2075 | 2450 |
|---|---|---|---|---|---|---|---|---|
| Conditions: | | | | | | | | |
| WHSV | 0.5 | 0.5 | 0.25 | 0.25 | 0.25 | 0.25 | 0.25 | 0.50 |
| H₂/Oil, molar | 5.0 | 5.0 | 4.5 | 2.8 | 2.5 | 1.8 | 1.8 | 1.0 |
| % w HCl in feed | 17.5 | 21 | 21 | 16 | 14 | 14 | 14 | 17 |
| Pressure, psig | 350 | 350 | 350 | 350 | 350 | 250 | 250 | 250 |
| Temp., ° F | 220 | 235 | 235 | 235 | 230 | 230 | 230 | 230 |
| Feed Composition, % w | | | | | | | | |
| Isopentane | 5 | 20 | 35 | 35 | 35 | 35 | 35 | 35 |
| n-Pentane | 95 | 80 | 55 | 55 | 55 | 55 | 55 | 55 |
| Unidentified | 0 | 0 | 0 | 0 | 0 | 0 | 0 | 0 |
| 2-Methylpentane | 0 | 0 | 0 | 0 | 0 | 0 | 0 | 0 |
| n-Hexane | 0 | 0 | 10 | 10 | 10 | 10 | 10 | 10 |
| Methylcyclopentane | 0.05 | 0 | 0.05 | 0.05 | 0.05 | 0.05 | 0.05 | 0 |
| Cyclohexane | 0 | 0 | 0 | 0 | 0 | 0 | 0 | 0 |
| Product Composition, % w | | | | | | | | |
| Cracked | 0.08 | 0.07 | 0.16 | 0.17 | 0.17 | 0.18 | 0.20 | 0.23 |

Table I-continued

| Time, hrs. after start | 300 | 500 | 950 | 1700 | 1750 | 1925 | 2075 | 2450 |
|---|---|---|---|---|---|---|---|---|
| Isopentane | 66.77 | 51.13 | 60.47 | 66.57 | 66.63 | 64.70 | 64.73 | 62.58 |
| n-Pentane | 32.89 | 48.58 | 27.38 | 22.56 | 22.18 | 24.18 | 23.53 | 27.60 |
| 2,2-Dimethylbutane | Trace | Trace | 4.12 | 4.26 | 4.45 | 4.32 | 4.57 | 3.71 |
| 2,3-Dimethylbutane | " | " | 1.25 | 1.15 | 1.11 | 1.11 | 1.17 | 1.07 |
| 2-Methylpentane | " | " | 3.50 | 2.91 | 2.99 | 3.01 | 3.13 | 2.70 |
| 3-Methylpentane | " | " | 1.83 | 1.51 | 1.56 | 1.58 | 1.64 | 1.37 |
| n-Hexane | " | " | 1.10 | 0.84 | 0.87 | 0.88 | 0.91 | 0.90 |
| Methylcyclopentane | " | " | 0.02 | 0.01 | 0.02 | 0.02 | 0.02 | 0 |
| Cyclohexane | " | " | 0.02 | 0.02 | 0.02 | 0.02 | 0.02 | 0 |
| % i-$C_5$ in $C_5$ | 56.7 | 51.28 | 68.8 | 74.7 | 75.0 | 72.8 | 73.3 | 69.4 |
| % DMB's in $C_6H_{14}$ | — | — | 45.5 | 50.3 | 50.7 | 49.8 | 50.3 | 49.8 |
| % MCP in $C_6H_{12}$ | — | — | 42.2 | 39.5 | 40.4 | 42.4 | 41.5 | — |
| $AlCl_3$ loss, ppmw, based on product | 22 | 15 | 5 | 3 | 3 | 3 | 3 | 2 |

On the basis of catalyst activity decline rates and $AlCl_3$ losses demonstrated in the above table, it appears that catalyst lifetimes of at least one year can be achieved with the catalysts of the instant invention in the absence of aluminum chloride make-up and scrubbing facilities.

Illustrative Embodiment III

The regeneration of catalyst paraffin isomerization activity was demonstrated for a catalyst according to the invention which had declined in activity after extended use in isomerization according to the general procedure described in Illustrative Embodiment II. The catalyst employed in this test was similar to that used in Illustrative Embodiment II — i.e., 18.4% by weight $MnCl_2/AlCl_3$ on alumina basis finished catalyst, at an $MnCl_2/AlCl_3$ weight ratio of unity — except the alumina support was chlorided (1.6% by weight Cl) with hydrochloric acid rather than $NiCl_2$. In this case, the isomerization start-up conditions were 220° F, 350 psig, 10.5 $H_2$/hydrocarbon (oil) mole ratio, 0.5 WHSV and 3.6% by weight HCl, basis feed. After 2000 hours run time at increasingly rigorous reaction conditions, the catalyst activity for isomerization had declined to a sufficient degree that regeneration was considered desirable. At this point, the isomerization reactant feed over the catalyst was discontinued and the following stepwise regeneration procedure was effected. Firstly, the catalyst was stripped for 18 hours at 220° F with $H_2$ at 0.8 SCF/hour to remove volatile hydrocarbons. Next the temperature of the catalyst was raised to 450° F and the catalyst was stripped for 10 hours with $H_2$ at 0.1–0.15 SCF/hour and HCl at 1.3 g/hour. At this point the $H_2$-gas strip was discontinued and stripping with HCl was further carried out for an additional 4.5 hours at the same conditions. Finally, the temperature of the catalyst was reduced to 220° F and the catalyst was swept with $H_2$ at 0.2 SCF/hour for 4 hours. The results of this test run, including the pertinent reaction variables before and after regeneration are recorded in Table II, below.

Table II

| Time, Hrs. After Start | Prior to Regeneration | | | After Regeneration | | | | |
|---|---|---|---|---|---|---|---|---|
| | 300 | 1900 | 2000 | 2001 | 2002 | 2020 | 2190 | 2486 |
| Conditions: | | | | | | | | |
| WHSV | 0.46 | 0.4 | 0.4 | 0.4 | 0.4 | 0.4 | 0.4 | 0.4 |
| $H_2$/Oil, Molar | 5.3 | 2.2 | 2.3 | 2 | 1.85 | 4.0 | 4.0 | 4.0 |
| %w HCl in feed | 6 | 11 | 10 | 10 | 10 | 9 | 10 | 10 |
| Pressure, psig | 350 | 350 | 350 | 350 | 350 | 350 | 350 | 350 |
| Temp., ° F | 220 | 220 | 220 | 220 | 220 | 220 | 220 | 220 |
| Feed Composition, %w | | | | | | | | |
| Isopentane | 33.53 | 31.67 | 33.29 | 33.29 | 33.29 | 33.29 | 31.73 | 33.60 |
| n-Pentane | 53.76 | 53.56 | 52.00 | 52.00 | 52.00 | 52.00 | 52.03 | 51.54 |
| Unidentified | 0.14 | 0.24 | 0.24 | 0.24 | 0.24 | 0.24 | 0.26 | 0.24 |
| 2-Methylpentane | 1.68 | 10.63 | 10.84 | 10.84 | 10.84 | 10.84 | 12.02 | 11.03 |
| n-Hexane | 9.60 | 0 | 0 | 0 | 0 | 0 | 0 | 0 |
| Methylcyclopentane | 0.53 | 1.56 | 1.14 | 1.14 | 1.14 | 1.14 | 1.58 | 1.43 |
| Cyclohexane | 0.75 | 2.34 | 2.49 | 2.49 | 2.49 | 2.49 | 2.38 | 2.15 |
| Product Composition, %w | | | | | | | | |
| Cracked | 0.07 | 0.13 | 0.09 | 0.34 | 0.36 | 0.07 | 0.05 | 0.04 |
| Isopentane | 53.43 | 48.66 | 46.97 | 67.82 | 67.03 | 47.64 | 43.87 | 42.98 |
| n-Pentane | 34.13 | 37.11 | 38.04 | 20.70 | 21.14 | 38.18 | 41.90 | 42.76 |
| 2,2-Dimethylbutane | 3.49 | 2.90 | 2.90 | 4.08 | 4.12 | 2.97 | 2.29 | 2.05 |
| 2,3-Dimethylbutane | 1.24 | 1.34 | 1.48 | 1.07 | 0.92 | 1.20 | 1.31 | 1.54 |
| 2-Methylpentane | 3.69 | 3.54 | 3.90 | 2.44 | 2.51 | 3.63 | 4.02 | 4.16 |
| 3-Methylpentane | 1.84 | 1.84 | 2.06 | 1.28 | 1.29 | 1.88 | 2.12 | 2.19 |
| n-Hexane | 1.18 | 1.04 | 1.15 | 0.67 | 0.67 | 1.07 | 1.10 | 1.05 |
| Methylcyclopentane | 0.41 | 1.37 | 1.36 | 0.66 | 0.73 | 1.26 | 1.27 | 1.29 |
| Cyclohexane | 0.62 | 2.07 | 2.05 | 0.94 | 1.03 | 1.89 | 1.86 | 1.94 |
| Unidentified | — | — | — | — | 0.20 | 0.21 | 0.21 | — |

Table II-continued

| Time, Hrs. After Start | Prior to Regeneration | | | After Regeneration | | | | |
|---|---|---|---|---|---|---|---|---|
| | 300 | 1900 | 2000 | 2001 | 2002 | 2020 | 2190 | 2486 |
| % i-C$_5$ | 61.0 | 56.72 | 55.25 | 71.07 | 76.02 | 55.5 | 51.51 | 50.11 |
| % DMB's in C$_6$H$_{14}$ | 41.7 | 39.77 | 38.13 | 53.96 | 53.75 | 39.87 | 34.50 | 32.62 |
| % n-Hexane in C$_6$H$_{14}$ | 10.4 | 9.76 | 10.03 | 6.97 | 7.08 | 9.78 | 9.93 | 9.56 |
| % MCP in C$_6$H$_{12}$ | 39.8 | 39.16 | 39.77 | 41.16 | 41.40 | 39.98 | 40.64 | 39.90 |
| % of Equilibrium Value | | | | | | | | |
| i-C$_5$ in C$_5$ | 74.5 | 69.3 | 67.5 | 86.8 | 92.8 | 67.8 | 62.9 | 61.2 |
| DMB's in C$_6$H$_{14}$ | 78.1 | 74.5 | 71.4 | 100 | 100 | 74.7 | 64.6 | 61.1 |

The results given in Table II indicate that substantial regeneration of catalysts according to the invention is attainable. The bottom two lines of the table show the percent of equilibrium value for isopentane in the pentanes and for dimethylbutanes in C$_6$ paraffins at 220° F. After 1,900–2,000 hours, 2.2 H$_2$/oil molar ratio and 10% by weight HCl in the feed gave only about a 72% approach to equilibrium. However, immediately after regeneration and under the same operation conditions, the conversion went to equilibrium. Reducing the severity of the reaction conditions by increasing the H$_2$/oil ratio from 2.2 to 4.0 resulted in the same conversion as obtained under more severe conditions just before regeneration. The sustained activity of the regenerated catalyst is illustrated in the 466 hour operating period following regeneration during which the catalyst activity decline was only 0.24% i-C$_5$/day.

Illustrative Embodiment IV

A fused bromide salt complex catalyst on a gamma-alumina support was prepared according to the procedure described in Method A of Illustrative Embodiment I and tested for isomerization activity utilizing the method described generally in Illustrative Embodiment II. In this test, the alumina support (40–80 mesh) was not pre-chlorided prior to deposition of the fused salt complex and the finished catalyst contained 52.8% by weight of a MnBr$_2$/AlBr$_3$ complex formed by combining MnBr$_2$ and AlBr$_3$ in a MnBr$_2$/AlBr$_3$ weight ratio of 1/2.87. The start-up conditions for the test included a reaction temperature of 220° F, a reactant feed rate of 0.29 WHSV, a reaction zone pressure of 350 psig, a H$_2$ to hydrocarbon (oil) mole ratio of 8.7 and 5.0% by weight HBr in the feed. The results of this test run, including the pertinent reaction variables are given in Table III, below.

Table III

| Time, hrs. after start | 1.75 | 18 | 19.25 | 24.5 |
|---|---|---|---|---|
| Conditions: | | | | |
| Hydrocarbon feed, g/hr | 10.0 | 10.0 | 10.0 | 10.0 |
| WHSV | 0.29 | 0.29 | 0.29 | 0.29 |
| H$_2$/Oil, Molar | 8.7 | 7.0 | 5.8 | 4.4 |
| %w HBr in feed | 5.0$^{(a)}$ | 5.0$^{(a)}$ | 5.0$^{(a)}$ | 5.0$^{(a)}$ |
| Pressure, psig | 350 | 350 | 350 | 350 |
| Temp., ° F | 220 | 220 | 220 | 220 |
| Feed Composition, %w | | | | |
| Isopentane | 34.47 | 34.47 | 34.47 | 34.47 |
| n-Pentane | 54.36 | 54.36 | 54.36 | 54.36 |
| Unidentified | 0.13 | 0.13 | 0.13 | 0.13 |
| 2-Methylpentane | 1.72 | 1.72 | 1.72 | 1.72 |
| n-Hexane | 9.32 | 9.32 | 9.32 | 9.32 |
| Product Composition, %w | | | | |
| Cracked | 0.01 | 0.10 | 0.10 | 0.12 |
| Isopentane | 34.80 | 47.59 | 50.79 | 51.44 |
| n-Pentane | 50.02 | 43.63 | 41.90 | 39.78 |
| 2,2-Dimethylbutane | 0.29 | 0.74 | 0.76 | 1.48 |
| 2,3-Dimethylbutane | 0.51 | 0.87 | 0.71 | 0.88 |
| 2-Methylbutane | 4.02 | 2.95 | 2.49 | 3.08 |
| 3-Methylpentane | 1.76 | 1.42 | 1.24 | 1.45 |
| n-Hexane | 8.59 | 2.70 | 2.01 | 1.77 |
| % i-C$_5$ in C$_5$ | 41.0 | 52.17 | 54.79 | 56.40 |
| % DMB's in C$_6$H$_{14}$ | 5.9 | 18.53 | 20.45 | 27.27 |

$^{(a)}$the 5.0%w HBr in the hydrocarbon feed corresponds on a molar basis to 2.25%w HCl.

Illustrative Embodiment V

The activity of the supported fused salt complex catalysts of the invention in promoting alkylation of isobutane with ethylene was demonstrated using the tubular microreactor and catalyst described in Illustrative Embodiment I. In this test, vapor phase alkylation was effected by passing a gaseous mixture containing isobutane/ethylene at 17/1 mole ratio at a space velocity of 1.8 WHSV basis total hydrocarbon over the catalyst at 350 psig and 150° F. Also present in the vapor feed to alkylation were H$_2$ at an H$_2$/total hydrocarbon molar ratio of 2.3 and HCl at a concentration of 1.2% by weight basis total hydrocarbon. These reaction conditions were maintained for the first 23 hours of the test run after which time the HCl concentration was increased to 3.0% by weight basis total hydrocarbon to increase the conversion of ethylene. The results of this test run including data taken at 2 hours after the increase in HCl concentration are given in Table IV below.

Table IV

| Hours after Start | Ethylene Conversion | Percent of Product | | | |
| --- | --- | --- | --- | --- | --- |
| | | 2,2-Dimethyl-butane | Ethyl Chloride | Total $C_6$ | Total $C_5/C_7$ |
| 3 | 100 | 5 | 9 | 36 | 55 |
| 7 | 97 | 20 | 12 | 49 | 39 |
| 10 | 94 | 28 | 14 | 54 | 32 |
| 23 | 72 | 55 | 27 | 66 | 7 |
| 25 | 89 | 47 | 32 | 62 | 6 |

From the results given in the table, it is apparent that the catalyst tested possesses significant activity for alkylation of isobutane to the desired high octane value, 2,3-dimethylbutane. This alkylation activity appears to increase and/or become more selective as the catalyst ages with a concomitant reduction in the formation of $C_5$ and $C_7$ hydrocarbons. It is thought that the $C_5/C_7$ hydrocarbon formation is due to polymerization or oligomerization of ethylene over the catalyst and consequent cracking of the polymers or oligomers formed.

What is claimed is:

1. A solid, particulate catalytic composition for hydrocarbon conversion reactions which comprises a fused salt complex of an aluminum halide selected from the class consisting of aluminum chloride, aluminum bromide and mixtures thereof and a manganous halide selected from the class consisting of manganous chloride, manganous bromide and mixtures thereof present on the surfaces of a porous, refractory inorganic oxide carrier; said solid catalytic composition being formed by heating a composite mixture of the halide salt components of the fused salt complex to a temperature above the melting point of the composite, depositing the melted composite on the carrier surfaces and cooling of the carrier containing the melted composite to a temperature below the melting point of the fused salt complex.

2. The catalytic composition according to claim 1, wherein the fused salt complex consists of 1–3 parts by weight of the aluminum halide and 3–1 parts by weight of the manganous halide.

3. The catalytic composition according to claim 2 wherein the aluminum halide is aluminum chloride and the manganous halide is manganous chloride.

4. The catalytic composition according to claim 2 wherein the aluminum halide is aluminum bromide and the manganous halide is manganous bromide.

5. The catalytic composition according to claim 2 wherein the fused salt complex consists of 1–1.5 parts by weight of the aluminum halide and 1.5–1 parts by weight of the manganous halide.

6. The catalytic composition according to claim 2 wherein the carrier is an alumina-containing material having a surface area in the range of 150–500 m²/g.

7. The catalytic composition according to claim 6 wherein the carrier is pre-chlorided such that it contains 0.5 to 5% by weight chloride ion based on carrier weight.

8. The catalyst composition according to claim 7 wherein the aluminum halide is aluminum chloride and the manganous halide is manganous chloride.

9. The catalyst composition according to claim 2 wherein the fused salt complex makes up about 10 to about 60% by weight of the finished catalyst.

10. The catalyst composition according to claim 3 wherein the fused salt complex makes up about 10 to about 50% by weight of the finished catalyst.

11. The catalyst composition according to claim 4 wherein the fused salt complex makes up about 40 to about 60% by weight of the finished catalyst.

12. The catalyst composition according to claim 8 wherein the carrier is a gamma alumina having a surface area in the range of 150–300 m²/g.

13. The catalyst composition according to claim 2 wherein a metal hydrogenation function selected from metals in Group VIII of the Periodic Table of Elements is incorporated into the catalyst composition.

14. The catalyst composition according to claim 13 wherein the metal hydrogenation function is present in the catalyst composition in a quantity ranging from about 0.1 to 10% by weight of the finished catalyst.

15. The catalyst composition according to claim 14 wherein the metal hydrogenation function is selected from the class consisting of nickel, cobalt and platinum.

* * * * *